United States Patent
Lee et al.

(10) Patent No.: US 6,278,958 B1
(45) Date of Patent: Aug. 21, 2001

(54) METHOD FOR PREDICTING A NOISE INTENSITY EMITTED FROM A FAN AND OR A PUMP

(75) Inventors: Duck Joo Lee, Seoul; Wan Ho Jeon, Incheon, both of (KR)

(73) Assignee: Korea Advanced Institute Science and Technology (KR)

(*) Notice: Subject to any disclaimer, the term of this patent is extended or adjusted under 35 U.S.C. 154(b) by 0 days.

(21) Appl. No.: 09/504,956

(22) Filed: Feb. 16, 2000

(30) Foreign Application Priority Data

Feb. 18, 1999 (KR) .................................................. 99-5341

(51) Int. Cl.[7] .................................................... G06F 11/32
(52) U.S. Cl. .......................... 702/183; 381/71.9; 73/649
(58) Field of Search ........................... 702/183; 381/71.9; 181/213; 73/649

(56) References Cited

U.S. PATENT DOCUMENTS

| 3,776,363 | * | 12/1973 | Kuethe | 181/213 |
| 5,010,576 | * | 4/1991 | Hill | 381/71.9 |
| 5,625,150 | * | 4/1997 | Greene et al. | 73/649 |

OTHER PUBLICATIONS

Seybert et al., "An Advanced Computational Method For Radiation And Scattering Of Acoustic Waves In Three Dimensions," *J. Acoust. Soc. Am.,* vol. 77, No. 2, pp. 362–368, (Feb. 1985).

Jeon et al., "An Analysis Of The Flow And Sound Fields Of A Centrifugal Fan Located Near A Wedge," 5th AIAA/CEAS Aeroacoustics Conference, pp. 1–10, (May 10–12, 1999).

Lohmann, "Prediction Of Ducted Radiator Fan Aeroacoustics With A Lifting Surface Method," DGLR/AIAA 92 92–02–098, pp. 576–588.

"Sysnoise Rev. 5.3," *Computational Vibro–Acoustics,* User's Manual vol. 2, pp. 356–365 and 396–399.

* cited by examiner

Primary Examiner—Kamini Shah
Assistant Examiner—Edward Raymond
(74) Attorney, Agent, or Firm—Akin, Gump, Strauss, Hauer & Feld, L.L.P.

(57) ABSTRACT

A method for predicting a noise intensity emitted from a fan is provided. The method in accordance with the present invention provides data about the performance of the fan and a noise intensity corresponding to a shape of the fan and operating conditions so that the data are used in design and manufacturing of fans. The method comprises following steps for: analyzing a flow field around the fan on the basis of a fan shape and operating conditions; obtaining a noise source value of the fan from force data of blades at a given time in the analyzed flow field; and calculating a noise intensity from the noise source value.

11 Claims, 3 Drawing Sheets

METHOD FOR PREDICTING A NOISE INTENSITY EMITTED FROM A FAN AND OR A PUMP

TECHNICAL FIELD

The present invention relates to a method for predicting a noise intensity emitted from a fan and/or a pump, more particularly, the method applied to a centrifugal fan and/or a pump.

BACKGROUND OF THE INVENTION

Though many companies are interested in noise prediction, not many studies have been performed in the area of noise prediction.

In order to control fan noise, one should be able to control performance and noise and accordingly shape of the fan needs to be modified. Low noise fan manufacturers should know how to perform experiments and how to analyze as well.

So far, any analysis method for centrifugal fan noise has not been reported because it requires not only understanding of complicated techniques but also combination of complicated techniques.

SUMMARY OF THE INVENTION

A method for fan noise prediction is provided. The method in accordance with the present invention generates performance and several noise values with fan shape and operating condition for design and manufacturing of fans.

In accordance with the present invention, the method for predicting a noise intensity emitted from a fan comprises steps for: analyzing a flow field around the fan on the basis of a fan shape and operating conditions; obtaining a noise source value of the fan from force data of blades at a given time in the analyzed flow field; and calculating a noise intensity from the noise source value.

In analyzing a flow field around the fan, data about the fan shape and the operating conditions are received, and then a flow field at every time with a vortex method in consideration of rotation of the fan analyzed.

Obtaining a noise source value of the fan comprises: reading data about the flow field along with data about the relevant fan and the relevant impeller; forming a noise source mesh over the relevant impeller or the relevant rotor, which are main sources of noise generated in the fan; calculating a sound pressure by acoustic analogy; determining whether a sound field is being analyzed in the domain of frequency or the domain of time; and calculating an observer time in consideration of a retarded time, and calculating noise source values at every time in consideration of the retarded time if the sound field is being analyzed in the domain of time, while converting the noise source values into that in the domain of frequency and obtaining a noise source value of a designated frequency from them if the sound field is being analyzed in the domain of frequency.

Calculating a sound pressure uses following Equation;

$$p - p_0 = \left[ \frac{x_i - y_i}{4\pi a_0^3 r^2 (1 - M_r)} \left\{ \frac{\partial F_i}{\partial t} + \frac{F_i}{1 - M_r} \frac{\partial M_r}{\partial t} \right\} \right],$$

in which sound density related with an acoustic pressure is represented by p, speed of sound by $a_0$, force data calculated from flow data, which is used as input data for noise source value calculation, by $F_i$, position of a noise source mesh by x, and position of force at impeller blades by y.

Calculating a noise intensity comprises: reading data about the shape of the fan and the noise source values, and then analyzing a sound field on the basis of the data; determining whether an acoustic pressure at a point is needed, or acoustic pressures through the sound field are needed; and providing the acoustic pressure at the point if it is needed, while forming a mesh through the sound field, and then calculating the acoustic pressures at each point in the mesh if they are needed.

Analyzing a sound field after reading data about the shape of the fan and the noise source values is performed using a noise source mesh.

Analyzing a sound field after reading data about the shape of the fan and the noise source values is performed by following Equation;

$$C(P)\phi(P) = \int_S \left[ \phi(Q) \frac{\partial G}{\partial n}(P, Q) - \frac{\partial \phi}{\partial n} G(P, Q) \right] dS(Q) +$$
$$\int_{Kirchhoff} \left[ \phi(K) \frac{\partial G}{\partial n}(P, K) - \frac{\partial \phi}{\partial n} G(P, K) \right] dS(K) +$$
$$\int_v Q_{SC}(X_{SC}) G(P, X_{SC}) dv,$$

in which $$\int_{Kirchhoff} \left[ \phi(K) \frac{\partial G}{\partial n}(P, K) - \frac{\partial \phi}{\partial n} G(P, K) \right] dS(K)$$

is a term supplied by sound mesh.

The method for predicting a noise intensity emitted from a fan in accordance with the present invention can be implemented in a computer system. Then, calculating a noise intensity from the noise source value can be performed using newly developed Kirchhoff-Helmholtz Boundary Element Method(BEM)with noise source mesh

BRIEF DESCRIPTION OF THE DRAWINGS

Several preferred embodiments of the fan noise prediction method in accordance with the present invention will be explained with reference to the accompanying drawings, in which.

DETAILED DESCRIPTION OF THE INVENTION

Figure 1:
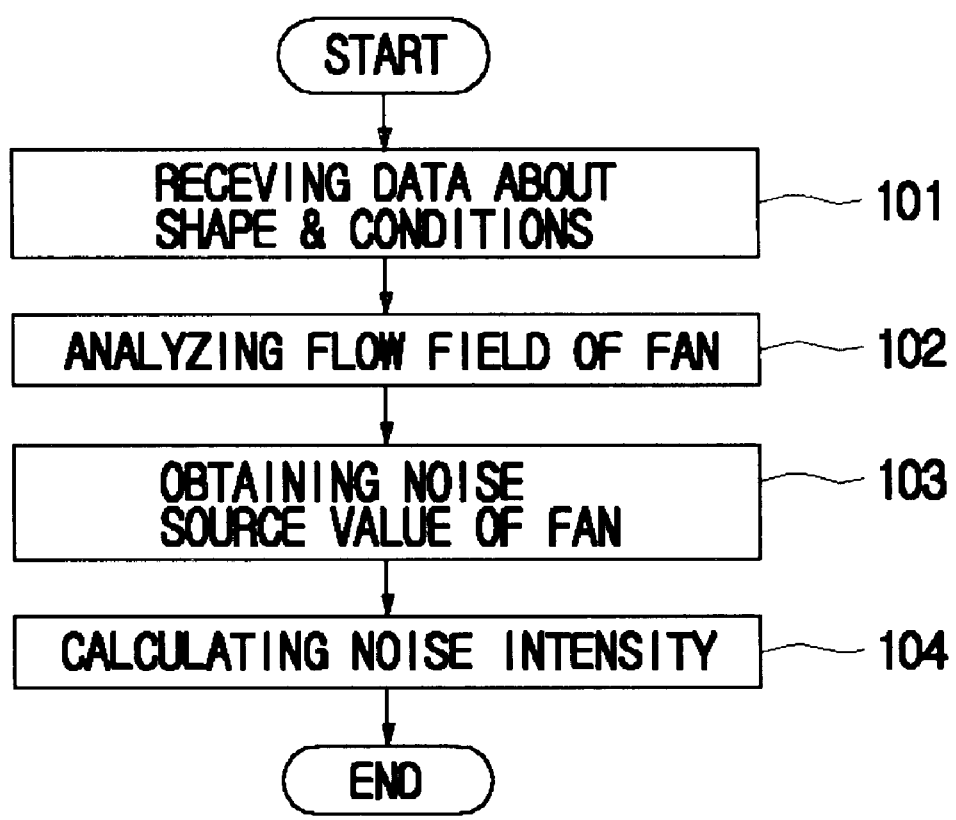
FIG. 1 is a flow diagram illustrating an embodiment of the fan noise prediction method in accordance with the present invention.

As shown in FIG. 1, in order to predict fan noise, it is required to receive data about a fan shape and operating conditions for flow analysis at Step 101.

Flow analysis is performed on the basis of the fan shape and the operating conditions, and then a flow field is defined at Step 102. Definition of the flow field is generally performed using CFD (Computation Fluid Dynamics) method. However, a flow field at every time can be easily analyzed by a vortex method in consideration of fan rotation.

A noise source value is obtained from blades force data of the defined flow field at Step 103, and the noise source value is stored.

Noise is predicted on the basis of the noise source value at Step 104. Fan noise at a selected position or at a selected time can be directly predicted on the basis of data of the noise source values.

Figure 2:
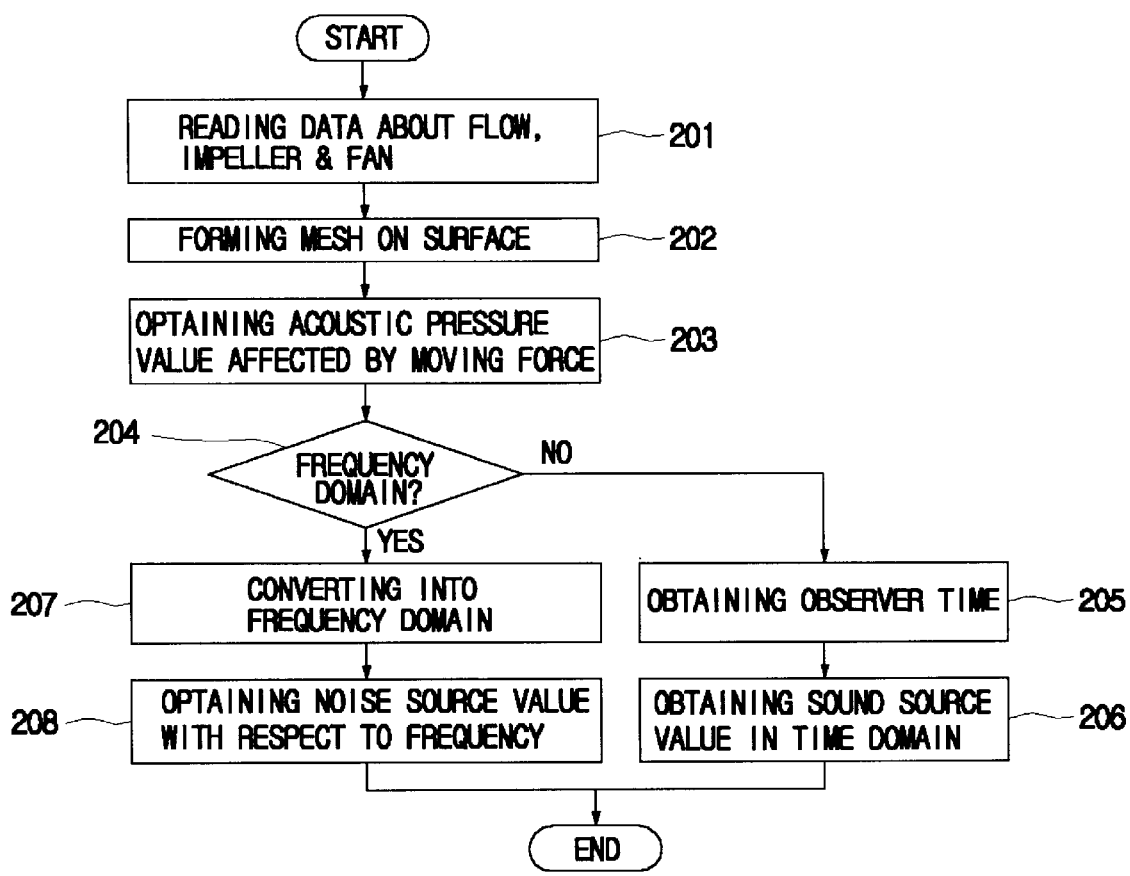
FIG. 2 is a flow diagram illustrating A noise source value calculation process in the method as shown in FIG. 1.

Referring to FIG. 2, a noise source value calculation process is explained

Firstly, the analyzed flow data are read along with information about an impeller and a fan related to them at Step 201. It is noted that all of the flow data regarding the impeller and the fan should be read, and that they represent force change at each blades of the impeller.

At Step 202, a mesh is made on the surface of impeller or rotor that acts as a noise source. The mesh is called noise source mesh and it is a Kirchhoff surface. A noise source value is calculated at each point of the mesh.

Next, at Step 203, an acoustic pressure is obtained on the basis of acoustic analogy using the aforementioned shape data and flow data that are analyzed at each point of the mesh. Analyzed result contains only characteristics of noise source values because this analogy is performed in an acoustic field, and then any shape information of the fan is not considered in the calculation.

Also, since the flow analysis and the acoustic analogy are performed in the domain of time, the noise source values are valid in the domain of time.

The acoustic analogy was developed by Lowson and following Equation 1 shows it.

$$\rho - \rho_0 = \left[\frac{x_i - y_i}{4\pi a_0^3 r^2 (1 - M_r)}\left\{\frac{\partial F_i}{\partial t} + \frac{F_i}{1 - M_r}\frac{\partial M_r}{\partial t}\right\}\right],$$ [Equation 1]

in which sound density related with an acoustic pressure is represented by p, speed of sound by $a_0$, force data calculated from flow data, which is used as input data for noise source value calculation, by $F_i$, position of a noise source mesh by x, and position of force at impeller blades by y.

After an acoustic pressure value of moving force is obtained at Step 203, it is determined whether an analyzing domain, at which the sound field is analyzed, is the domain of frequency or the domain of time at Step 204.

If the analyzing domain is the domain of time, an observer time is obtained in consideration of a retarded time at points of mesh at Step 205. Then, the noise source values of the domain of time are calculated in consideration of retarded time and stored at Step 206.

If the analyzing domain is the domain of frequency, the noise source values of the surface are converted into that of the domain of frequency 207. Then, a noise source value of the designated frequency is obtained from the noise source values of the surface at Step 208, which were converted into the domain of frequency. FFT (Fast Fourier Transform) method is used for such conversion.

Size of the data gets bigger because the noise source values exist in all frequency range.

Although the noise source values of all frequencies are calculated at every point of the noise source mesh for the sound field of a designated frequency, a process for calculating a sound field using them requires reading and searching large-sized files.

Therefore, only the value of the designated frequency is stored.

Figure 3:
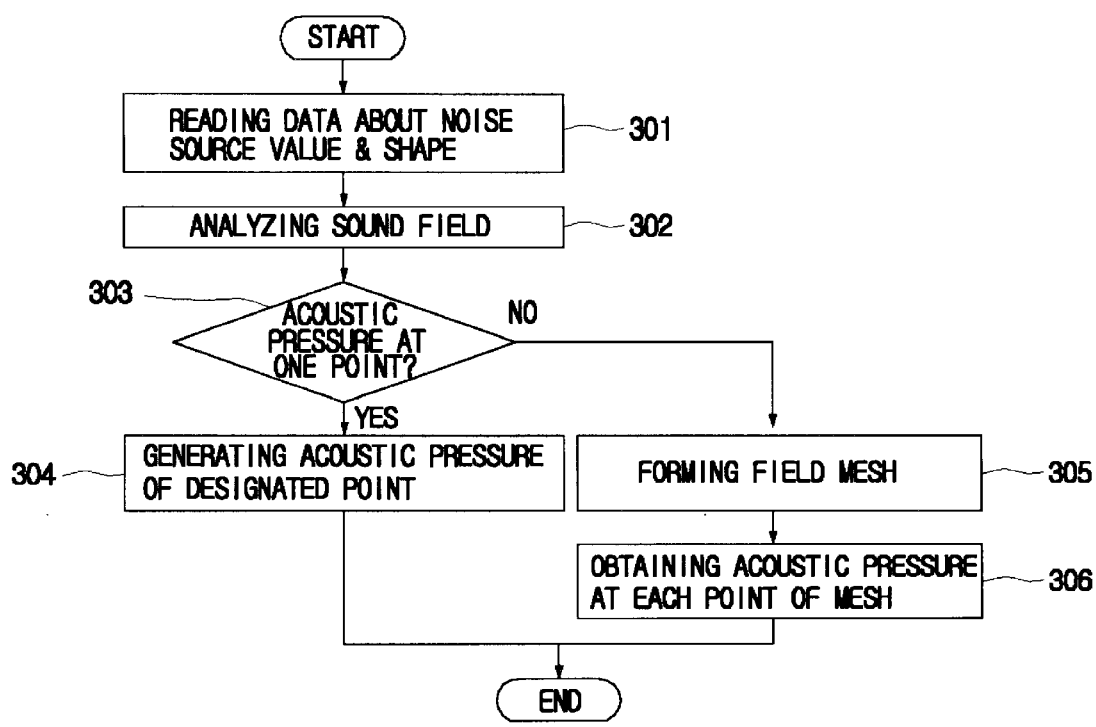
FIG. 3 is a flow diagram illustrating a noise prediction process in the method as shown in FIG. 1.

FIG. 3 is a flow diagram illustrating the noise prediction process of FIG. 1.

As shown in FIG. 3, the calculated noise source values and the fan shape are read at Step 301.

The sound field is analyzed on the basis of the noise source values and the fan shape at Step 302.

Generally, a wave equation is analyzed by BEM (boundary element method) or FEM (finite element method). In this embodiment, BEM is used.

Equation 2 shows a basic equation of BEM.

$$C(P)\phi(P) = \int_S\left[\phi(Q)\frac{\partial G}{\partial n}(P, Q) - \frac{\partial \phi}{\partial n}G(P, Q)\right]dS(Q) +$$ [Equation 2]

$$\int_v Q_{SC}(X_{SC})G(P, X_{SC})dv$$

The last term of equation 2 have a value, for example, monopole or dipole, which is usually used as a noise source in BEM.

However, a general BEM is not able to consider the noise source of fans.

Equation 3 shows a Kirchhoff-Helmholtz BEM equation having newly derived sound mesh as a noise source.

$$C(P)\phi(P) = \int_S\left[\phi(Q)\frac{\partial G}{\partial n}(P, Q) - \frac{\partial \phi}{\partial n}G(P, Q)\right]dS(Q) +$$ [Equation 3]

$$\int_{Kirchhoff}\left[\phi(K)\frac{\partial G}{\partial n}(P, K) - \frac{\partial \phi}{\partial n}G(P, K)\right]dS(K) +$$

$$\int_v Q_{SC}(X_{SC})G(P, X_{SC})dv,$$

in which $$\int_{Kirchhoff}\left[\phi(K)\frac{\partial G}{\partial n}(P, K) - \frac{\partial \phi}{\partial n}G(P, K)\right]dS(K)$$

is a tem supplied by sound mesh,

After the sound field is analyzed, it is determined whether a sound pressure at one point is needed, or all of the sound pressures in the sound field are needed at Step 303.

If a sound pressure at one point is needed, only the required sound pressure is supplied at Step 304. Otherwise, a mesh over the field is generated at Step 305 and then a sound pressure at each point of the mesh is obtained at Step 306.

The fan noise prediction method in accordance with the present invention provides efficient ways to predict a fan noise when a fan shape and operating conditions are available.

In addition, the fan noise prediction method in accordance with the present invention is helpful to manufacture a low noise fans and provides ways of analysis for saving development costs.

Although the present invention is explained with preferred embodiments, it should be understood that they are only for illustrating other than limiting the invention. Those who are skilled in the art, to which the invention is attributed, will appreciate that various modifications, alterations and modulations are possible without departing from the scope and spirit of the present invention as defined in the accompanying claims.

What is claimed is:

1. A method for predicting a noise intensity emitted from a fan, comprising steps for:

analyzing a flow field around the fan on the basis of a fan shape and operating conditions;

obtaining a noise source value of the fan from force data of blades at a given time in the analyzed flow field; and calculating a noise intensity from the noise source value;

wherein said step for analyzing a flow field around the fan further comprises receiving data about the fan shape and the operating conditions and analyzing a flow field at every time with a vortex method in consideration of rotation of the fan; and wherein said step for obtaining a noise source value of the fan further comprises the steps for:

reading data about the flow field along with data about the relevant fan and the relevant impeller;

forming a noise source mesh over that relevant impeller or the relevant roter, which are main sources of noise generated in the fan;

calculating a sound pressure by acoustic analogy;

determining whether a sound field is being analyzed in the domain of frequency or the domain of time; and calculating an observer time in consideration of a retarded time, and calculating noise source values at every time in consideration of the retarded time if the sound field is being analyzed in the domain of time, while converting the noise source values into that in the domain of frequency and obtaining a noise source value of a designated frequency from them if the sound field is being analyzed in the domain of frequency.

2. The method for predicting a noise intensity emitted from a fan according to claim 1, wherein said step for calculating a sound pressure uses following equation;

$$\rho - \rho_0 = \left[\frac{x_i - y_i}{4\pi a_0^3 r^2 (1-M_r)} \left\{ \frac{\partial F_i}{\partial t} + \frac{F_i}{1-M_r} \frac{\partial M_r}{\partial t} \right\} \right],$$

in which sound density related with an acoustic pressure is represented by p, speed of sound by $a_0$, force data calculated from flow data, which is used as input data for noise source value calcuation, by $F_i$, psotion of a noise source mesh by x, and postion of force at impeller blades by y.

3. The method for predicting a noise intensity emitted from a fan according to claim 1, wherein said step for calculating a noise intensity comprises the steps for:
   reading data about the shape of the fan and the noise source values, and then analyzing a sound field on the basis of the data;
   determining whether an acoustic pressure at a point is needed, or acoustic pressures through the sound field are needed; and
   providing the acoustic pressure at the point if it is needed, while forming a mesh through the sound field, and then calculating the acoustic pressures at each point in the mesh if they are needed.

4. The method for predicting a noise intensity emitted from a fan according to claim 3, wherein said step for analyzing a sound field after reading data about the shape of the fan and the noise source values is performed using a noise source mesh.

5. The method for predicting a noise intensity emitted from a fan according to claim 4, wherein said step for analyzing a sound field after reading data about the shape of the fan and the noise source values is performed by following Equation.

$$C(P)\phi(P) = \int_S \left[\phi(Q)\frac{\partial G}{\partial n}(P,Q) - \frac{\partial \phi}{\partial n}G(P,Q)\right]dS(Q) +$$
$$\int_{Kirchhoff} \left[\phi(K)\frac{\partial G}{\partial n}(P,K) - \frac{\partial \phi}{\partial n}G(P,K)\right]dS(K) +$$
$$\int_v Q_{SC}(X_{SC})G(P,X_{SC})dv,$$

in which $$\int_{Kirchhoff} \left[\phi(K)\frac{\partial G}{\partial n}(P,K) - \frac{\partial \phi}{\partial n}G(P,K)\right]dS(K)$$

is a term supplied by sound mesh.

6. A method for fan noise prediction, comprising the steps of:
   analyzing the flow field of the fan on the basis of fan shape and operating conditions;
   reading fan data, impeller data, and analyzed flow field data of said fan;
   forming a source mesh on sound source surfaces of the fan;
   calculating sound pressure values by acoustic analogy;
   determining whether the frequency domain or time domain is used for sound field analysis;
   calculating an observer time in consideration of retarded time and sound source valve of every hour in consid-
   eration of retarded time when the time domain is used for sound field analysis;
   converting the source values of the surfaces into the frequency domain and calculating the source value of a designated frequency from the converted source value when the frequency domain is used for sound field analysis; and
   predicting fan noise using Kirchhoff-Helmholtz Boundary Element Method (BEM) with source mesh.

7. The method for fan noise prediction according to claim 6, wherein the step for analyzing the flow field of the fan further comprises; receiving data about the fan shape and operating conditions, and analyzing a flow field at every time with a vortex method in consideration of rotation of the fan.

8. The method for fan noise prediction of claim 6, wherein said step of calculating sound pressure values uses following equation:

$$\rho - \rho_0 = \left[\frac{x_i - y_i}{4\pi a_0^3 r^2 (1-M_r)} \left\{ \frac{\partial F_i}{\partial t} + \frac{F_i}{1-M_r} \frac{\partial M_r}{\partial t} \right\} \right]$$

wherein p represents sound density, related with acoustic pressure; $a_p$ represents the speed of sound; $F_i$ represents force data calculated from flow data, used as input data for source value calculation; x represents the position of the source mesh; and y represents the position of force at the impeller blades.

9. The method for fan noise prediction of claim 6, wherein the step of predicting fan noise comprises the steps of:
   reading the fan shape and the source values and analyzing the sound field on the basis of the fan shape and the source values;
   determining whether the acoustic pressure of one point or of the sound field is needed;
   providing the acoustic pressure of the one point if the acoustic pressure of one point is needed; and
   forming a mesh of the sound field and calculating acoustic pressures at each point of the mesh if the acoustic pressure of the sound field is needed.

10. The method for fan noise prediction of claim 9, wherein the step of reading the fan shape employs sound mesh in analyzing the sound field.

11. The method for fan noise prediction of claim 9, wherein the step of reading the fan shape employs the following equation in analyzing the sound field:

$$C(P)\phi(P) = \int_S \left[\phi(Q)\frac{\partial G}{\partial n}(P,Q) - \frac{\partial \phi}{\partial n}G(P,Q)\right]dS(Q) +$$
$$\int_{Kirchhoff} \left[\phi(K)\frac{\partial G}{\partial n}(P,K) - \frac{\partial \phi}{\partial n}G(P,K)\right]dS(K) +$$
$$\int_v Q_{SC}(X_{SC})G(P,X_{SC})dv,$$

in which $$\int_{Kirchhoff} \left[\phi(K)\frac{\partial G}{\partial n}(P,K) - \frac{\partial \phi}{\partial n}G(P,K)\right]dS(K)$$

is a term supplied by the sound mesh.

* * * * *